United States Patent [19]

Carnahan et al.

[11] Patent Number: 5,686,415
[45] Date of Patent: Nov. 11, 1997

[54] METHOD FOR THE TREATMENT OF COLON EPITHELIAL CELLS IN VIVO

[75] Inventors: Josette Françoise Carnahan, Newbury Park; Shinichi Hara; Hsieng Sen Lu, both of Thousand Oaks, all of Calif.; John Philip Mayer, Boulder, Colo.; Steven Kiyoshi Yoshinaga, Thousand Oaks, Calif.

[73] Assignee: Amgen Inc., Thousand Oaks, Calif.

[21] Appl. No.: 760,815

[22] Filed: Dec. 5, 1996

Related U.S. Application Data

[62] Division of Ser. No. 417,640, Apr. 6, 1995, Pat. No. 5,670,342.

[51] Int. Cl.$^6$ .......................... C07K 13/00; C12N 15/12; C12N 1/21; A61K 37/02
[52] U.S. Cl. .............. 514/12; 514/21; 530/350; 530/399; 530/389.2; 435/69.1
[58] Field of Search .................. 514/12, 21; 530/350, 530/399, 389.2; 435/69.1

[56] References Cited

FOREIGN PATENT DOCUMENTS

| WO 94/00140 | 1/1994 | WIPO . |
| 9428133 | 8/1994 | WIPO . |
| WO 94/28133 | 12/1994 | WIPO . |

OTHER PUBLICATIONS

Peles et al., Cell, vol. 69, pp. 205–216 (1992).
Holmes et al., Science, vol. 256, pp. 1205–1210 (1992).
Marchionni et al., Nature, vol. 362, pp. 312–318 (1993).
Falls et al., Cell, vol. 72, pp. 801–815 (1993).
Orr–Urtreger et al., Proc. Natl. Acad. Sci. USA, vol. 90, pp. 1867–1871 (1993).
Wen et al., Mol. and Cell. Biol., vol. 14, No. 3, pp. 1909–1919 (1994).
Wen et al., Cell, vol. 69, pp. 559–572 (1992).
Bacus et al. Cancer Research, vol. 53, pp. 5251–5261 (1993).
Kita et al., FEBS Letters, vol. 349, pp. 139–143 (1994).
Plowman et al., Nature, vol. 366, pp. 473–475 (1993).
Carraway et al., Journal of Biological Chemistry, vol. 269, No. 19, pp. 14303–14306 (1994).
Carraway et al., Cell, vol. 78, pp. 5–8 (1994).
Bacus et al., Cell Growth & Differentiation, vol. 3, pp. 401–411 (1992).

*Primary Examiner*—Cecilia J. Tsang
*Assistant Examiner*—P. L. Touzeau
*Attorney, Agent, or Firm*—Steven M. Odre; Ron K. Levy; Richard J. Mazza

[57] ABSTRACT

Colon epithelial cells are stimulated to multiply, grow and mature by contacting them in vivo with peptides derived from the EGF-like domain of proteins of the NDF/heregulin family.

5 Claims, 5 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 52 amino acids ( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

```
Ser His Leu Val Lys Cys Ala Glu Lys Glu Lys Thr Phe Cys Val Asn
 1               5                  10                      15
Gly Gly Glu Cys Phe Met Val Lys Asp Leu Ser Asn Pro Ser Arg Tyr
                20                  25                  30
Leu Cys Lys Cys Gln Pro Gly Phe Thr Gly Ala Arg Cys Gln Asn Tyr
            35              40                  45
Val Met Ala Ser
         50
```

( 2 ) INFORMATION FOR SEQ ID NO:2:

( i ) SEQUENCE CHARACTERISTICS:
( A ) LENGTH: 52 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:2:

```
Ser His Leu Val Lys Cys Ala Glu Lys Glu Lys Thr Phe Cys Val Asn
 1               5                  10                      15
Gly Gly Glu Cys Phe Met Val Lys Asp Leu Ser Asn Pro Ser Arg Tyr
                20                  25                  30
Leu Cys Lys Cys Pro Asn Glu Phe Thr Gly Asp Arg Cys Gln Asn Tyr
            35              40                  45
Val Met Ala Ser
         50
```

( 2 ) INFORMATION FOR SEQ ID NO:3:

( i ) SEQUENCE CHARACTERISTICS:
( A ) LENGTH: 52 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:3:

```
Ser His Leu Val Lys Cys Ala Glu Lys Glu Lys Thr Phe Cys Val Asn
 1               5                  10                      15
Gly Gly Glu Cys Phe Met Val Lys Asp Leu Ser Asn Pro Ser Arg Tyr
                20                  25                  30
Leu Cys Lys Cys Gln Pro Gly Phe Thr Gly Ala Arg Cys Thr Glu Asn
            35              40                  45
Val Pro Met Lys
         50
```

( 2 ) INFORMATION FOR SEQ ID NO:4:

( i ) SEQUENCE CHARACTERISTICS:
( A ) LENGTH: 52 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:4:

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Thr Glu Asn
        35                  40                  45

Val Pro Met Lys
    50

( 2 ) INFORMATION FOR SEQ ID NO:5:

( i ) SEQUENCE CHARACTERISTICS:
      ( A ) LENGTH: 40 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:5:

Cys Ala Glu Lys Glu Lys Thr Phe Cys Val Asn Gly Gly Glu Cys Phe
1               5                   10                  15

Met Val Lys Asp Leu Ser Asn Pro Ser Arg Tyr Leu Cys Lys Cys Gln
            20                  25                  30

Pro Gly Phe Thr Gly Ala Arg Cys
        35              40

( 2 ) INFORMATION FOR SEQ ID NO:6:

( i ) SEQUENCE CHARACTERISTICS:
      ( A ) LENGTH: 40 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:6:

Cys Ala Glu Lys Glu Lys Thr Phe Cys Val Asn Gly Gly Glu Cys Phe
1               5                   10                  15

Met Val Lys Asp Leu Ser Asn Pro Ser Arg Tyr Leu Cys Lys Cys Pro
            20                  25                  30

Asn Glu Phe Thr Gly Asp Arg Cys
        35              40

METHOD FOR THE TREATMENT OF COLON EPITHELIAL CELLS IN VIVO

This application is a division of application Ser. No. 08/417,640, filed Apr. 6, 1995, now U.S. Pat. No. 5,670,342 which is hereby incorporated by reference.

FIELD OF THE INVENTION

This invention relates to novel peptides derived from polypeptides of the so-called NDF/heregulin family. These peptides exhibit biological properties as a mitogenic and differentiation factor for colon epithelial cells and as a trophic and mitogenic factor for Schwann cells.

BACKGROUND OF THE INVENTION

The protein called neu differentiation factor, or "NDF", is a 44-kilodalton polypeptide originally isolated from rat fibroblasts which has been shown to induce the growth or differentiation of epithelial cells; Peles et al., *Cell*, Volume 69, pages 205–216 (1992). Both this heat-stable rodent protein and its human homolog, called heregulin, are secreted proteins that were originally purified by heparin-binding chromatography from the media of cultured cancer cells; Peles et al., *Cell*, above, and Holmes et al., *Science*, Volume 256, pages 1205–1210 (1992). Several glial cell growth factors (GGF) isolated from bovine brain tissue have been found to be related to these so-called NDF/heregulins; Marchionni et al., *Nature*, Volume 362, pages 312–318 (1993). Similarly, a group of proteins called ARIA, ranging in molecular weight from 33 to 44 kilodaltons and purified from chicken brain tissue on the basis of their acetylcholine receptor inducing activity, have been shown to be structurally related to the NDF/heregulins; Falls et al., *Cell*, Volume 72, pages 801–815 (1993). The NDF/heregulin family of proteins is now known to contain at least twelve distinct molecules. It has been reported that the human homolog members of this family are encoded by a single gene, located on human chromosome $8p^{12}\text{-}p^{21}$, which contains at least 13 exons whose precise organization has not been determined; Orr-Urtreger et al., Proceedings of the National Academy of Science, USA, Volume 90, pages 1867–1871 (1993).

The cell membrane-bound precursor forms of these proteins (referred to in this description as "proNDF/heregulins") are mosaics of recognizable structural motifs. They include an N-terminal hydrophobic Signal peptide, followed by either a so-called "kringle" domain (consisting of about 250 amino acid residues) or an N-terminal non-hydrophobic sequence (consisting of about 40 amino acid residues). Other regions include an immunoglobulin(Ig)-like domain (approximately 70 amino acid residues), a so-called "spacer" domain that contains multiple binding sites for N- and O-linked glycosylation, an epidermal growth factor (EGF)-like domain of about 60–75 amino acid residues that includes 6 cysteine residues, a hydrophobic region of about 25 amino acid residues that functions as a transmembrane domain, and a "cytoplasmic tail" which can vary in length. Some of these transmembranous precursor forms undergo proteolytic cleavage in the cell at both the N-terminus and at the short stretch of sequence (juxtamembrane) that connects the EGF-like domain with the transmembrane domain. Depending on the amino acid sequence in this juxtamembrane region, the NDF/heregulins have been designated subtype 1, subtype 2, subtype 3, etc. Additional variations comprise two forms of the C-terminal loop of the EGF-like domain, which are termed alpha($\alpha$) and beta($\beta$), depending on the amino and sequence in this region; Wen et al., *Molecular and Cellular Biology*, Volume 14, Number 3, pages 1909–1919 (1994).

Originally isolated as a family of molecules that induce phosphorylation of tyrosine residues in the erbB2/Her2 proto-oncogene expression product, the NDF/heregulins were thought at first to be a possible ligand for that receptor; Peles et al., *Cell*, above; Wen et al., *Cell*, Volume 69, pages 559–572 (1992); Holmes et al., *Science*, above, and Bacus et al., *Cancer Research*, Volume 53, pages 5251–5261 (1993). However, it has more recently been shown that the NDF/heregulins bind to and stimulate the receptor proteins encoded by the genes known as erbB3/Her3 and erbB4/Her4; Plowman et al., Volume 366, pages 473–475 (1993); Kita et al., *FEBS Letters*, Volume 349, pages 139–143 (1994); Carraway et al., *The Journal of Biological Chemistry*, Volume 269, Number 19, pages 14303–14306 (1994); and Carraway et al., *Cell*, Volume 78, pages 5–8 (1994). The EGF-like domains of the various NDF/heregulins appear to be responsible for receptor recognition and act independently of other structural motifs; see Holmes et al., *Science*, above.

In vitro, NDF/heregulins have been found to be weakly mitogenic for various epithelial cells, including mammary, lung and gastric epithelial cells; Holmes et al., *Science*, above. However, certain mammary tumor cells apparently undergo growth arrest in response to NDF or its human homolog; Peles et al., *Cell*, above; and Bacus et al., *Cell Growth and Differentiation*, Volume 3, pages 401–411 (1992). Treated cells exhibit a mature phenotype which includes a flat morphology, synthesis of the intracellular cell adhesion molecule ICAM-1, and in the case of mammary cells, the secretion of milk components; Bacus et al., *Cell Growth and Differentiation*, above; and Bacus et al., *Cancer Research*, above. Recombinantly produced glial growth factors (GGFs) have been observed to be mitogenic for cultured Schwann cells, which otherwise divide very slowly even in the presence of known mitogenic factors; see Marchionni et al., *Nature*, above. The motor-neuron derived NDF/heregulin family member known as ARIA appears to induce the synthesis of acetylcholine receptors, and possibly other molecules, by post-synaptic muscle cells; see Falls, *Cell*, above.

SUMMARY OF THE INVENTION

Based on studies conducted with regard to localization of the N- and C-terminal ends of the extracellular ("soluble") portion of membrane-bound NDF/heregulin polypeptides, a putative C-terminal processing site has been assigned to these polypeptides. This C-terminal end has been incorporated into the design of two shorter-length forms of the polypeptides directed specifically to the EGF-like domain. These peptides, which are biologically active and comprise an aspect of the present invention, have the following amino acid sequences, respectively:

SHLVKCAEKEKTFCVNGGECFMVKDL-SNPSRYLCKCQPGFTGARCQNYVMAS (SEQ ID NO: 1), and

SHLVKCAEKEKTFCVNGGECFMVKDL-SNPSRYLCKCPNEFTGDRCQNYVMAS (SEQ ID NO:2)

The present invention additionally comprises DNA molecules encoding these peptides, expression vectors for directing the expression of the encoded peptides in host cells, transformed or transfected eukaryotic and prokaryotic host cells useful in the production of the peptides, a method for the recombinant production of the peptides, methods of use for the peptides in the ex vivo treatment of cells and in human therapy, and compositions containing the peptides as a biologically active component.

This invention is based on the discovery of an important subregion within the known EGF-like domain of extracellular NDF-hereguilns, this subregion residing near the C-terminal end and extending from amino acid residue 222 to amino acid residue 228 of extracellular NDF/heregulin (corresponding to the amino acid sequence numbering of published PCT application WO 94/28133, as explained in greater detail further below). More specifically, it has now been recognized that the seven amino acid residue sequence from 222 to 228 in the β form of extracellular NDF/hereguilns confers greater biological activity in the assays shown here than the corresponding sequence from the α form of extracellular NDF/hereguilns, despite sequence identity in the rest of the molecule. This recognition has enabled the design and construction of biologically active peptides that are capable of duplicating the physiological effects of the longer length NDF/hereguilns, while potentially enabling greater ease of delivery in certain therapeutic administrations because of their smaller size.

Moreover, as will be seen from the biological results presented further below, the peptides of this invention are useful in appropriately effective amounts as human colon epithelial and Schwann cell growth factors, possessing the ability to stimulate the proliferation and maturation of such cells. Accordingly, these peptides are utilizable as nutrients for the survival and study of such cells in culture, and potentially as therapeutic agents for the treatment of diseases or conditions resulting from deficiencies, deterioration or abnormalities of such cells in the body.

DETAILED DESCRIPTION OF THE INVENTION

Figure 1:
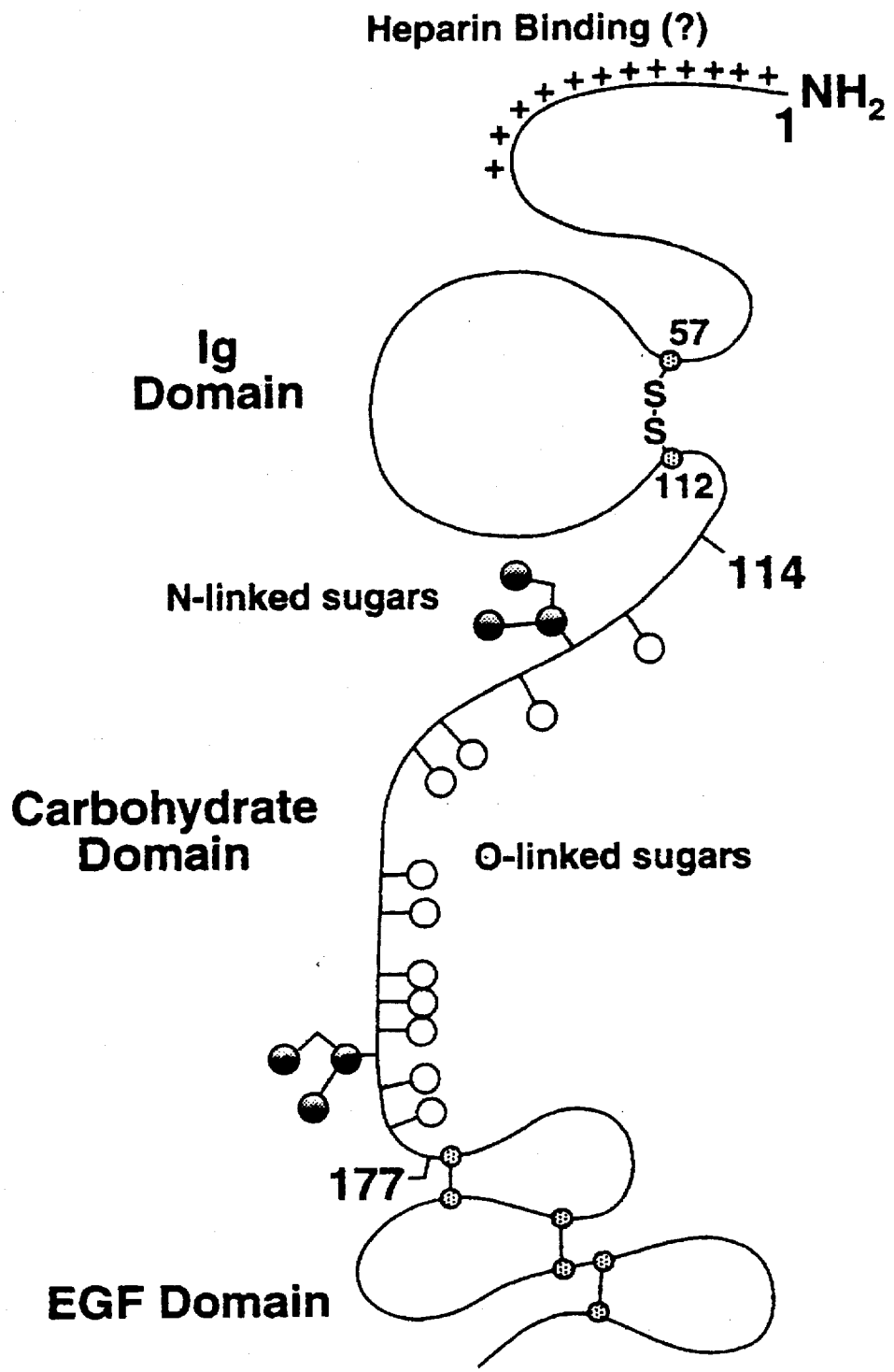
FIG. 1. This figure is a schematic drawing (not in proportional scale) of the extracellular structure of human NDF/heregulin, comprising (distal from the end that binds to the cell membrane): the putative N-terminal "heparin-binding" region, an immunoglobulin (Ig)-like domain, a carbohydrate (or "spacer") domain, and an EGF-like domain proximal to the C-terminal end. The open circles in the spacer domain represent O-linked sugars and the branched closed circles represent N-linked sugars. Four disulfide bonds, one of which is in the Ig-like domain and three of which are in the EGF-like domain, are also shown. Numbers designate amino acid residue positions at selected points along the polypeptide chain, starting sequentially from the N-terminal end and moving towards the C-terminal end. The EGF-like domain begins approximately at amino acid residue position 177 (marked) and ends approximately at amino acid residue position 228 (not marked).

Studies undertaken with respect to cDNAs for α and β forms of extracellular NDF/heregulin, as expressed in Chinese hamster ovary (CHO) cells, have succeeded in localizing the C-terminal end at amino acid residue 228 as the primary site for proteolytic cleavage. Using the particular NDF/hereguilns known as α2 and β1, several peptides were designed based on identity with or homology to the EGF-like domains in these proteins. As used here, the proteins referred to as "α2" and "β1" are those which have been disclosed in PCT application WO 94/28133, published Dec. 8, 1994. The sequence of α2 (from amino acid residue 1 to amino acid residue 462) is given in FIG. 32 of the PCT application (see also SEQ ID NO: 8 therein). The sequence of β1 is given partially (from amino acid residue 95 to amino acid residue 645) in FIG. 35 of the published PCT application (see also SEQ ID NO. 14 therein). The first ninety four amino acid residues (N-terminal end) of β1, not depicted in PCT FIG. 35, are identical to the first ninety four amino acid residues of α2 shown in PCT FIG. 32. A depiction of the extracellular ("soluble") portion of the α and β forms of NDF/heregulin is shown in FIG. 1 of the present description.

The initial studies referred to here utilized peptides based solely on sequences of the EGF-like domain of the aforementioned α2 and β1 forms of NDF/heregulin, that is to say, that portion of the extracellular protein from amino acid residue 177 to amino acid residue 228 (see FIG. 1 herein). Studies revealed that the β peptide, referred to herein as EGF-β, was more biologically active than the α peptide (EGF-α) in certain assays. The reason for this difference was not initially apparent. However, during peptide mapping studies of the EGF-like domains of NDF/hereguilns, it was discovered that the α and β forms cleaved (degraded) at different rates when subjected to digestion by endoproteinase Lys-C. Specifically, the β form was more resistant to this enzyme and cleaved at a slower rate. Moreover, this phenomenon seemed limited to the lysine residue at position 211. There was no apparent difference in the rate of cleavage between α and β at any other lysine residues in the N-terminal end of the EGF-like domain. This observation suggested that the structural conformation of the region of the molecule containing lysine-211 may differ between α and β, leading to faster enzymatic cleavage for the α form.

Further, it was noted that the amino acid sequence in the EGF-like domain of the α and β forms are identical from amino acid residue position 177 to amino acid residue position 212. It was surmised that the difference in susceptibility to cleavage must be due to conformational differences in the C-terminal end of the EGF-like domain, from amino acid residue 212 to amino acid residue 228. This rationale suggested that the C-terminal end may be critical for biological activity and prompted the synthesis of two chimeras for further testing and confirmation of this hypothesis. Specifically, these two chimeric peptides were based on "switching" the 222–228 amino acid sequence between EGF-α and EGF-β, in order to study the effect on biological activity of this sequence. In all, four peptides were synthesized, including the aforementioned two chimeric peptides. The four peptides had the following sequences:
(1) SHLVK (A) QNYVMAS, or EGF-α/β (SEQ ID NO:1)
(2) SHLVK (B) QNYVMAS, or EGF-β (SEQ ID NO:2)
(3) SHLVK (A) TENVPMK, or EGF-α (SEQ ID NO:3)
(4) SHLVK (B) TENVPMK, or EGF-β/α (SEQ ID NO:4)
in which
  "(A)" denotes the amino acid sequence CAEKEKT-FCVNGGECFMVKDLSNPSRYLCKCQPGFTGARC (SEQ ID NO:5), and
  "(B)" denotes the amino acid sequence CAEKEKT-FCVNGGECFMVKDLSNPSRYLCKCPNEFTGDRC (SEQ ID NO:6).

The relatively short length of these peptides lended itself to preparation by chemical synthesis, utilizing the following method.

Chemical Synthesis of Peptides

Each peptide was prepared by the Fmoc (fluorenylmethoxycarbonyl)/t-butyl-based solid phase chemistry method for peptide synthesis. An ABI-431 instrument (Applied Biosystems, Foster City, Calif.), with a single coupling program, was utilized to effect peptide chain assembly starting with a commercially available hydroxymethyl-phenylacetyl (HMP) derivatized polystyrene resin. The dicyclohexyl carbodiimide (DDC) mediated coupling of the C-terminal residue, FmocLys(t-Boc)OH, was catalyzed with 4-dimethylaminopyridine (DMAP). All of the subsequent residues were coupled either as symmetrical anhydrides or hydroxybenztriazole (HOBt) esters. Upon completion of the synthesis, each peptide resin was vacuum dried overnight, then subjected to acidolytic deprotection and cleavage using 20 ml of a mixture comprising trifluoroacetic acid:thioanisole:β-mercaptoethanol:water:phenol in a ratio of 80:5:5:5:5, respectively. After stirring for four hours at room temperature, the suspension was filtered, the filtrate was concentrated (using a rotary evaporator), and the crude peptide was precipitated using cold diethyl ether.

The peptide was immediately suspended in 50 ml of an 8M guanidine buffer containing 100 mM of dithiothreitol (DTT) and 50 mM of TRIS, adjusted to pH 8. After stirring for several hours at room temperature, the solution was applied to a Vydac $C_4$ preparative reverse phase column and eluted with a 0–60% gradient of 0.1% TFA/acetonitrile over one hour, using a Beckman model 114M solvent delivery system. Fractions with the best analytical profile were pooled and lyophilized.

Optimal conditions for peptide folding to obtain an active product comprised dissolving the linear material (at approximately 1 mg/ml) in a buffer consisting of 25 mM of TRIS, pH 8, 1 mM of EDTA, 1 mM (for α forms) or 0.5 mM (for β forms) of glutathione (oxidized) and 1 mM of glutathione (reduced), and stirring overnight at room temperature. The oxidized, folded material was isolated using a preparative reverse phase column (YMC Co., Ltd., Japan) equipped with a thermostat jacket equilibrated at 40° C. and eluting with a shallow 0.1% TFA/acetonitrile gradient.

The homogeneity of the final products was assessed by analytical HPLC and CZE. Complete characterization was provided by amino acid analysis, electrospray mass spectrometry, partial preview sequencing, and enzymatic fragmentation.

Figure 2:
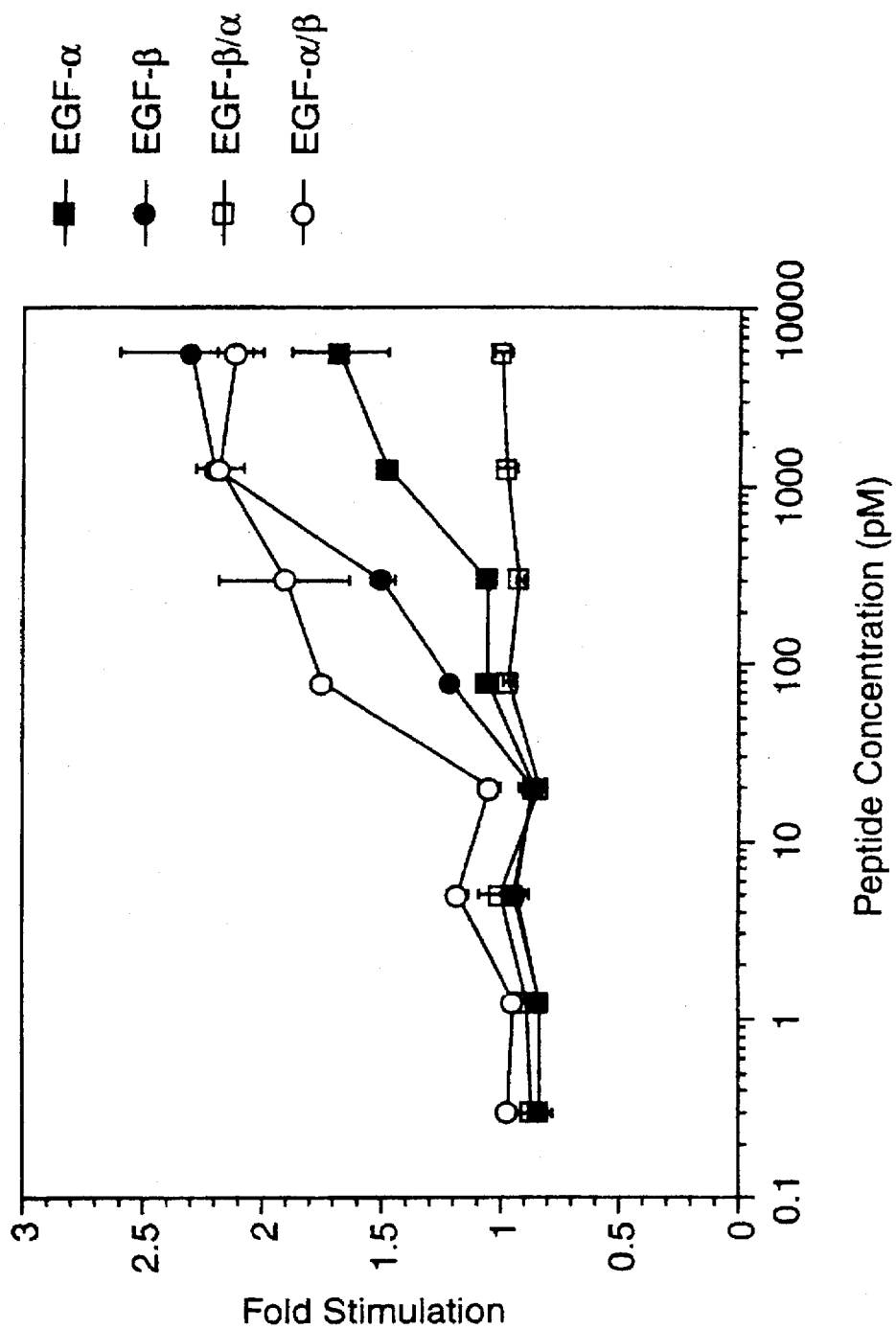
FIG. 2. This figure is a graphical representation of the proliferative effect of the peptides of the invention on human colonic epithelial cells in vitro. These peptides are designated in the figure as EGF-β (SEQ ID NO: 2, above), represented by the closed circles, and as EGF-α/β (SEQ ID NO: 1, above), represented by the open circles. For comparison, two other peptides of equal length are included, designated as EGF-α and EGF-β/α, and represented by the closed squares and open squares, respectively. The latter two are homologs based on the EGF domain of extracellular NDF-hereguilns and consist of the amino acid sequences shown further below in this text (SEQ ID NOS: 3 and 4, respectively). Proliferation is measured with a crystal violet dye which stains the cell protein and is indicative of cell number. The results are displayed on the vertical axis in units of fold stimulation, which is the absorbance of peptide-treated cells divided by the absorbance of untreated cells. The picomolar (pM) concentration of peptide used to treat the cells is shown on the horizontal axis. The best results for cell proliferation are seen with EGF-β and EGF-α/β, in accordance with the invention. Some proliferation was obtained with EGF-α, although it is clearly inferior to EGF-β and EGF-α/β. No effect was seen with EGF-β/α.

Colon Cell Proliferation a) Crystal Violet Proliferation Assay. The human colon epithelial cell line, LIM 1215 (Whitehead, R. H. et al., *J. Natl. Cancer Inst.* 4:759–765, 1985) was grown in RPMI-1640 media supplemented with 5% FBS, 1 µg/ml of hydrocortisone, 1 µg/ml of bovine insulin, 10 µM of alpha thioglycerol, and 1×PSG (0.292 mg/ml of 1-glutamine, 100 units/ml of penicillin G, and 100 µg/ml of streptomycin sulfate). At the start of the assay, the cells were 30% confluent and were proliferating rapidly. Cells were released by trypsin, washed with PBS, and seeded into 96-well plates at 5000 cells/well in low serum (0.05%) media (McCoy's-5A supplemented with 4 µg/ml of transferrin, 10 µg/ml of insulin, 10 mM of selenic acid, 4 nM of triiodothyronine, and 0.03% BSA). Dilutions of test peptide were added immediately on day zero; the total volume was 100 µl. Controls included no treatment and serial dilutions of FBS. The 96-well plates were then incubated for three days at 37° C. in a 5% $CO_2$ atmosphere. The media were removed by aspiration and 30 µl of 2% crystal violet (Difco) in methanol was added to the cells for fifteen minutes of staining. Excess dye was washed away with distilled water. To each well 100 µl of 0.04 N HCL in isopropanol was added and the dye was resolubilized by mixing. Absorbance was determined at 595 nm and the values were plotted as fold-stimulation over background (or no treatment).

b) Stimulation of colon cell proliferation LIM 1215 cells were treated with the above mentioned peptides, and the results are shown in FIG. 2. As shown in the figure, EGF-β stimulated the proliferation of LIM 1215 cells, while EGF-α was not as potent a mitogen. This strongly suggests that a powerful determinant of mitogenic activity resides in the last sixteen amino acids of the C-terminal portion of EGF-β corresponding to amino acids 213–228 of the full length extracellular NDF/heregulin referred to above. The chimeric peptides helped to pinpoint this determinant of activity to the seven residues corresponding to amino acids 222–228 of full length extracellular NDF/heregulin. Specifically, EGF-α/β consists of the first forty-five amino acid residues from the N-terminal portion of EGF-α and the last seven amino acid residues from the C-terminal portion of EGF-β (or α177–221/β222–228 corresponding to the amino acid numbering of full length extracellular NDF/heregulin). Conversely, EGF-β/α consists of the first forty-five amino acid residues from the N-terminal portion of EGF-β and the last seven amino acid residues from the C-terminal portion of EGF-α (or β177–221/α222–228 corresponding to the amino acid numbering of full length extracellular NDF/heregulin). While EGF-α/β displayed significant mitogenic activity on LIM 1215 colon cells, EGF-β/α did not show any detectable effect under the same conditions (see FIG. 2). These results demonstrate very clearly that the mitogenic activity of the peptides resides in the C-terminal end of the peptide. More specifically, the greatest degree of activity is attributable to the last seven amino acid residues from the EGF-like domain of the β form.

c) Staining of LIM 1215 human colon cells with fluorescent dye. LIM 1215 cells were grown in RPMI-1640 media supplemented with 5% FBS, 1 µg/ml of bovine insulin, 10 µm of alpha thioglycerol, and 1×PSG. At the time of assay, the cells were more than 30% confluent and were proliferating rapidly. The cells were seeded into 24-well plates at 25,000 cells/well in serum-free media (McCoy's-5A, supplemented with 4 µg/ml of transferrin, 10 µg/ml of insulin, 10 mM of selenic acid, 4 mM of triiodothyronine, and 0.03% BSA). Test peptides were added at a concentration of 420 picomolar immediately on day zero; the total volume was 1.0 ml. Controls included no treatment and serial dilutions of FBS. The 24-well plates were then incubated for three days at 37° C. and 5% $CO_2$, after which the media were removed by aspiration and the cells were washed in 1.0 ml of PBS with 0.5% BSA. All subsequent washings were performed with this buffer. The cells were then fixed in Orthopermeafix (Ortho Chemicals Co.) for thirty minutes at room temperature, and were washed twice. Then 200 µl of a 10 nM NBD phalloidin fluorescent dye solution in PBS were added and the cells were incubated in the dark (wrapped in aluminum foil) for thirty minutes at room temperature. The cells were washed twice, and inspected using a confocal microscope.

d) Morphogenic activity of peptides on colon epithelial cells. Upon treatment of LIM 1215 cells with the EGF-β peptide, it was evident that the morphology of the cells changed dramatically. FIG. 3 shows the staining of the actin filaments of the cells (see above for procedure) after no treatment (upper panel) and after treatment with 5% FBS (lower panel). In the absence of treatment, the cells appeared small and rounded. In the presence of FBS, the cells changed appearance, becoming only slightly larger but remaining rounded. In contrast, in the presence of EGF-β (FIG. 4, lower panel) the cells underwent a noticeable change in morphology, becoming enlarged and assuming a cobblestone-like appearance. On the other hand, EGF-α (FIG. 4, upper panel) did not produce the same morphogenic changes. Because the cells were proliferating rapidly in 5% FBS serum-containing media (FIG. 3), the unique morphology caused by the EGF-β peptide could not have been due solely to its ability to stimulate proliferation. Moreover, the difference in morphogenic activities between EGF-β and EGF-α must have originated in the last sixteen amino acids of the C-terminus, as this is the only difference in sequence between the two peptides.

Further localization of morphogenic activity was obtained by use of the chimeric peptides, EGF-β/α and EGF-α/β. As seen from FIG. 5, EGF-α/β caused apparent morphogenic changes in LIM 1215 cell (lower panel), while EGF-β/α did not produce any noticeable change (upper panel). Again, the only difference in sequence between these two peptides is the last seven amino acids of the C-terminal portion.

Additional confirmation of the importance of this seven amino-acid sequence was obtained by scoring for various marker proteins on the LIM 1215 cells. An ACAS confocal image cytometer was used to detect a number of markers on the cells without detaching the cells from the culture dish, as is normally done for fluorescence activated cell sorting (FACS) analysis. The data presented in Table 1, below, show that EGF-β caused increased expression (+) of carcinoembryonic antigen (CEA) and integrin β4. Conversely, villin expression was down-regulated (−) by EGF-β. The expression of a number of other markers was unchanged (0) by treatment with EGF-β. Analogous to the previous results characterizing gross, observable morphology changes, neither EGF-α nor EGF-β/α changed the levels of these marker proteins, while EGF-α/β changed the expression of the marker proteins in a manner similar to that seen with EGF-β.

TABLE 1

| Marker Protein | Marker Protein Expression | | | |
|---|---|---|---|---|
| | EGF-α | EGF-β | EGF-α/β | EGF-β/α |
| CEA | 0 | + | + | 0 |
| Integrin β4 | 0 | + | + | 0 |
| Villin | 0 | − | − | 0 |

Cancer treatments involving chemo- or radiation-therapy result in severe destruction of the epithelial layer of the colon. The foregoing results indicate that the peptides of the invention can promote re-epithelialization of the colon and alleviate the negative effects caused by damage to the intestinal epithelia.

Schwann Cell Survival and Proliferation

The neurobiological activity of the peptides was also evaluated by studying their effect on Schwann cell survival and growth, as described below.

The sciatic nerve from neonatal rats was used to generate a primary culture of Schwann cells. The cells were plated overnight in 10% serum without exposure to any growth factor. The following day, EGF-β, EGF-α/β and EGF-β/α were added at the concentrations in nanograms per milliliter (ng/ml) shown in Table 2, below. Twenty four hours later, BrdU was added to each test sample for six hours. BrdU is a thymidine analog which is incorporated into the DNA of dividing cells and can be detected by standard immunochemistry procedures. This agent thus provides a means for determining expansion of the total amount of DNA in a test sample and is a measure of whether cell proliferation has occurred. Upon the completion of the test period, Schwann cells were fixed and analyzed immunohistochemically. The cells were first stained for nerve growth factor receptor (NGFR), which is a known marker for Schwann cells in culture, followed by staining for BrdU. Cell counting was carried out as follows: in a given microscope field of view, all recognizable Schwann cells were counted, then the number of cells showing positive for BrdU staining were also counted. For each test sample (or well) two or three fields were counted, amounting to about 200 to 300 Schwann cells in all. The result is expressed in Table 2 as the percent of Schwann cells proliferating.

TABLE 2

| Peptide Concentration, ng/ml | Schwann Cell Proliferation | | |
|---|---|---|---|
| | EGF-β | EGF-α/β | EGF-β/α |
| 0 | 1 | 1 | 1 |
| 0.1 | 7.5 | 1 | 1 |
| 1 | 13 | 10 | 2 |
| 10 | 14 | 10 | 5 |
| 100 | 19 | 17 | 10 |

As can be seen from these results, both EGF-β and EGF-α/β stimulated the proliferation of Schwann cells to a significantly greater extent than EGF-β/α.

The test results presented above with respect to EGF-β and EGF-α/β indicate the usefulness of these peptides as agents for the survival, growth and proliferation of colon epithelial cells and Schwann cells. As a minimum, these peptides will be utilizable to grow such cells in culture for study in research, and further, for the production of tissue for use in implantation therapy with patients in need thereof. Of particular interest will be patients suffering from conditions or diseases involving deficiencies in, or losses of, such cells. In the case of colon epithelial cells in particular, such conditions include ulcers and colitis, both of which involve deficits in, or deterioration of, colon epithelial cells. The peptides of this invention offer promise as growth factors for the therapeutic treatment of such conditions, whether employed ex vivo to grow replacement tissue or used in vivo for the in situ production of such cells and tissues.

In the peripheral nervous system, Schwann cells, which constitute a class of glial cell, are responsible for the formation of the myelin sheath surrounding and insulating axons in vertebrates. The functional importance of myelin has been underscored by severe impairments in motor function observed in so-called demyelinating diseases, including multiple sclerosis and amyotrophic lateral sclerosis, which are associated with extensive degeneration of the mylein sheath in the central nervous system. Traumatic injury to the peripheral nervous system often involves destruction of myelin which must be repaired for proper healing. As the results shown demonstrate, the peptides of this invention are useful to support the survival, growth and proliferation of Schwann cells in culture, thus enabling a source of such cells for implantation into demyelinated sites of peripheral nerve damage. It is also possible that in vivo administration of these peptides, properly formulated, will result in the regeneration and proliferation of replacement Schwann cells, leading to remyelination and wound healing.

Utilization of the peptides of this invention in accordance with the aforementioned methods of application are well within the ability of the skilled practitioner. The amount of peptide effective for the treatment of a particular disorder or condition in vivo will depend on the specific nature of the disorder or condition, and such amounts can be determined by standard clinical techniques. Where possible, it is desirable to determine the dose-response curve and pharmaceutical compositions of the invention first in vitro, such as in known bioassay systems, and then in useful animal model systems prior to testing humans. Methods of in vivo administration include but are not necessarily limited to intravenous, intramuscular, intraperitoneal, oral or intradermal.

Further, it may be desirable to administer the pharmaceutical compositions of the invention locally to the area in need of treatment. This may be achieved, for example, by local infusion during surgery, injection, catheter, or implant, the implant being of a porous, non-porous, or gelatinous material, including membranes, such as sialastic membranes, or fibers.

The invention also provides for pharmaceutical compositions comprising peptides administered via liposomes, microparticles, or microcapsules. In various embodiments of the invention, it may be useful to use such compositions to achieve sustained release. The peptides of the invention may be administered in any sterile biocompatible carrier, including, but not limited to, saline, buffered saline, dextrose and water, as such, or, if desired, together with any suitable additives.

While the production of the peptides has been specifically illustrated with respect to chemical synthesis, conventional methods of recombinant production provide a suitable alternate means for their preparation. By way of illustration, a nucleotide sequence encoding the peptide can be inserted into an appropriate expression vector, i.e., a vector containing the necessary elements for the transcription and translation of the inserted peptide-coding sequence. A variety of host-vector systems may be utilized to express the peptide-encoding sequence. Such systems include but are not limited to mammalian cell systems infected with virus (e.g., vaccine virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of these vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate control signals and peptide coding sequences. These methods may include in vitro recombinant DNA and synthetic techniques and in vivo recombinations (genetic recombination). Expression of nucleic acid sequence encoding the peptide may be regulated by a second nucleic acid sequence so that the peptide is expressed in a host transformed with the recombinant DNA molecule. For example, expression may be controlled by any promoter/enhancer element known in the art.

Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

The resulting expressed peptide may be isolated and purified by standard methods, including chromatography (e.g., ion exchange, affinity, or sizing chromatography), centrifugation, differential solubility, or by any other standard technique for such purification.

The methods of recombinant production described in the previously mentioned PCT application WO 94/28133 are particularly suitable for use herein.

---

What is claimed is:

1. A method for causing the proliferation, growth and differentiation of colon epithelial cells comprising contacting such cells in vivo with an effective amount of a peptide having an amino acid sequence selected from the group consisting of:

SHLVKCAEKEKTFCVNGGECFMVKDL-SNPSRYLCKCQPGFTGARCQNY VMAS (SEQ. ID NO: 1) and

SHLVKCAEKEKTFCVNGGECFMVKDL-SNPSRYLCKCPNEFTGDRCO NYVMAS (SEQ. ID NO: 2).

2. The method according to claim 1 which is used for treating a disease or disorder of the colon.

3. The method according to claim 2 in which the disease or disorder in colitis.

4. The method according to claim 2 in which the disease or disorder is an ulcer.

5. The method according to claim 1 which is used for promoting re-epithelialization of the colon.

* * * * *

UNITED STATES PATENT AND TRADEMARK OFFICE
CERTIFICATE OF CORRECTION

PATENT NO. : 5,686,415
DATED : November 11, 1997
INVENTOR(S) : Hara, et al.

Figure 3A:
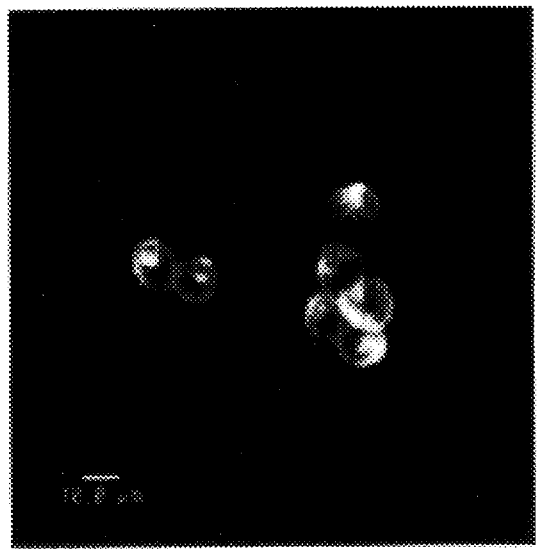
FIG. 3. This figure comprises microphotographs of fluorescently labeled actin in LIM 1215 human colon epithelial cells, either without treatment (upper panel) or with incubation for three days with 5% fetal bovine serum (FBS, lower panel). In the absence of treatment (upper panel), the cells appeared small and rounded. The cells showed some change with FBS treatment, and they appear slightly larger.
Figure 3B:
Figure 4A:
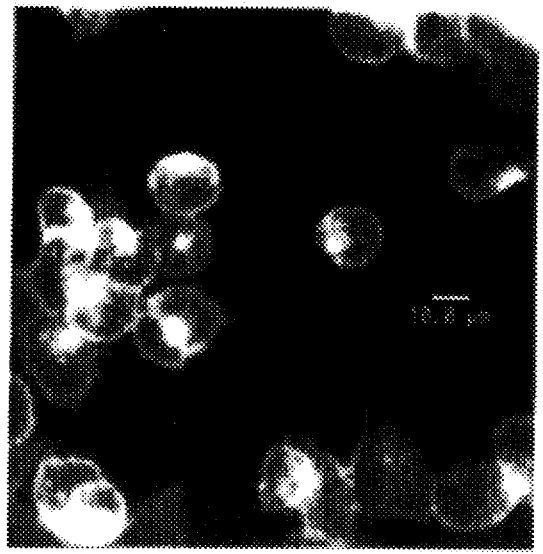
FIG. 4. This figure comprises microphotographs of fluorescently labeled actin in LIM 1215 human colon epithelial cells, following incubation for three days with EGF-α (comparison, upper panel) and EGF-β (this invention lower panel). Evidence of cellular morphological changes is seen for those cells treated with EGF-β, but not in cells treated with EGF-α. All peptides were added at a 420 picomolar concentration.
Figure 4B:
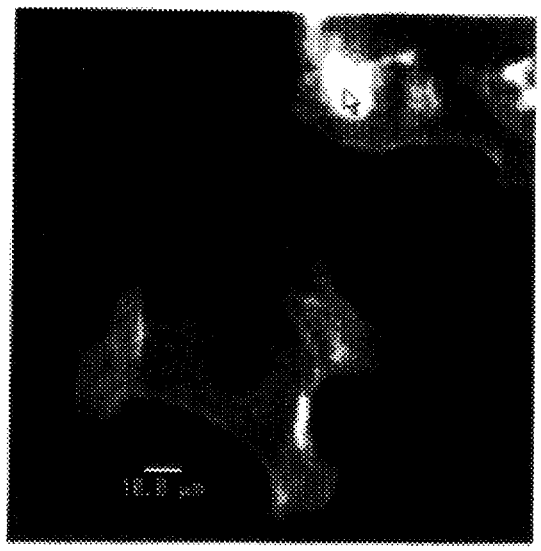
Figure 5A:
FIG. 5. This figure comprises microphotographs of flurosencently labeled actin in LIM 1215 human colon epithelial cells following incubation for three days with EGF-β/α (comparison, upper panel) and EGF-α/β (this invention, lower panel). As with EGF-β (FIG. 4, above), evidence of cell development and maturation is seen for cells treated with EGF-α/β. In contrast, those cells treated with EGF-β/α appear unchanged. All peptides were added at a 420 picomolar concentration.
Figure 5B:

It is certified that error appears in the above-identified patent and that said Letters Patent is hereby corrected as shown below:

title page, item [75], inventors, delete "Josette Francoise Carnahan, Newbury Park";

column 7, line 36, replace "(upper panel)" with -- FIG. 3A--;

column 7, line 37, replace "(lower panel)" with -- FIG. 3B--;

column 7, lines 40 and 41, replace "(FIG. 4, lower panel)" with -- FIG. 4B--;

column 7, line 44, replace "(FIG. 4, upper panel)" with -- FIG. 4A--;

column 7, line 56, replace "(lower panel)" with -- FIG. 5B--;

column 7, line 57, replace "(upper panel)" with -- FIG. 5A--;

column 9, line 24, replace "mylein" with -- myelin--; and column 14, line 57, replace "in" with -- is--.

Signed and Sealed this

Twenty-fifth Day of August, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.   : 5,686,415
DATED        : November 11, 1997
INVENTOR(S)  : Hara et al.

It is certified that error appears in the above-identified patent and that said Letters Patent is hereby corrected as shown below:

Title page,
Item [75], Inventors, delete "Josette Francoise Carnahan, Newbury Park";

Column 7,
Line 36, replace "(upper panel)" with -- FIG. 3A --;
Line 37, replace "(lower panel)" with -- FIG. 3B --;
Lines 40 and 41, replace "(FIG. 4, lower panel)" with -- FIG. 4B --;
Line 44, replace "(FIG. 4, upper panel)" with -- FIG. 4A --;
Line 56, replace "(lower panel)" with -- FIG. 5B --;
Line 57, replace "(upper panel)" with -- FIG. 5A --;

Column 9,
Line 24, replace "mylein" with -- myelin --; and

Column 14,
Line 57, replace "in" with -- is --.

Signed and Sealed this

Tenth Day of September, 2002

*Attest:*

JAMES E. ROGAN
*Director of the United States Patent and Trademark Office*

*Attesting Officer*